United States Patent [19]

Edwards et al.

[11] Patent Number: 5,336,482

[45] Date of Patent: Aug. 9, 1994

[54] TECHNETIUM-99M COMPLEXES WITH N-SUBSTITUTED 3-HYDROXY-4-PYRIDINONES

[75] Inventors: David S. Edwards, Burlington, Mass.; Christopher E. R. Orvig, Vancouver, Canada; Michael J. Poirier, Nashua, N.H.

[73] Assignee: The Du Pont Merck Pharmaceutical Company, Wilmington, Del.

[21] Appl. No.: 804,315

[22] Filed: Dec. 5, 1991

[51] Int. Cl.$^5$ .............................................. A61K 49/02
[52] U.S. Cl. ..................................... 424/1.65; 534/14
[58] Field of Search .................... 424/1.1, 1.65; 534/14

[56] References Cited

U.S. PATENT DOCUMENTS

| | | | |
|---|---|---|---|
| 3,981,980 | 9/1976 | Baker et al. | 424/1.1 |
| 4,193,979 | 3/1980 | Frank et al. | 424/1.1 |
| 4,440,739 | 4/1984 | Azuma et al. | 424/1.1 |
| 4,443,426 | 4/1984 | Thakur | 424/1.1 |
| 4,714,065 | 12/1987 | Feld et al. | 424/1.1 |
| 4,764,598 | 8/1988 | Srivastava et al. | 424/1.1 X |
| 4,830,847 | 5/1989 | Benedict et al. | 424/1.1 |
| 4,842,845 | 6/1989 | Rocklage et al. | 424/1.1 |
| 5,011,913 | 4/1991 | Benedict et al. | 424/1.1 X |

FOREIGN PATENT DOCUMENTS

WO9114664 10/1991 PCT Int'l Appl. .
2101118 1/1983 United Kingdom .

OTHER PUBLICATIONS

Finnegan et al., *J. Amer. Chem. Soc.* 1986, 108:5033–5035.
Kontoghiorghes et al., *Inorganica Chimica Acta.* 1987, 136:L11–L12.
Finnegan et al., *Inorg. Chem.* 1987, 26:2171–2176.
Nelson et al., *J. Am. Chem. Soc.* 1987, 109:4121–4123.
Nelson et al., *Inorg. Chem.* 1988, 27:1045–1051.
Matsuba et al., *Inorg. Chem.* 1988, 27:3935–3939.
Clevette et al., *Inorg. Chem.* 1989, 28:2079–2081.
Nelson et al., *Inorg. Chem.* 1989, 28:3153–3157.
Clevette et al., *Inorg. Chem.* 1990, 29:667–672.
Zhang et al., *Inorg. Chem.* 1991, 30:509–515.
Kanvinde et al., *J. Nuclear Med.* 1990, 31:908, Abst. No. 866.
Kavinde et al., "Cationic Complexes of Tc–99m–Hydroxy–4–pyrones ...", Abstract Medi #42, *Abstracts of Reports at Meeting of ACS Medicinal Chemistry Division,* 1991.

*Primary Examiner*—Robert L. Stoll
*Assistant Examiner*—John M. Covert
*Attorney, Agent, or Firm*—Blair Q. Ferguson; Gerald J. Boudreaux

[57] ABSTRACT

Disclosed are cationic complexes of Tc-99m and ligands having the structure:

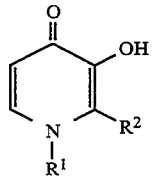

wherein:
R$^1$ is hydrogen or is selected from the group consisting of C$_1$ to C$_{20}$ alkyl; C$_3$ to C$_{12}$ cycloalkyl; C$_7$ to C$_{24}$ aralkyl; C$_2$ to C$_{16}$ alkyl ethers, thioethers, ketones or esters; C$_7$ to C$_{27}$ aralkyl ethers;

R$^2$ is hydrogen or is a C$_1$ to C$_4$ lower alkyl radical selected from the group consisting of methyl, ethyl, propyl, isopropyl, butyl, isobutyl, sec-butyl and tert-butyl.

10 Claims, No Drawings

TECHNETIUM-99M COMPLEXES WITH N-SUBSTITUTED 3-HYDROXY-4-PYRIDINONES

BACKGROUND OF THE INVENTION

The present invention is directed to cationic radiopharmaceutical complexes of technetium-99m (Tc-99m or $^{99m}$Tc) and particularly to cationic complexes of Tc-99m with N-substituted 3-hydroxy-4-pyridinones. Such cationic complexes are useful in diagnostic scintigraphic imaging.

Other heterocyclic complexes of radioactive metals have previously been reported in patents and scientific literature. For example:

Baker et al., in U.S. Pat. No. 3,981,980, disclose a diagnostic substance for cholescintigraphy which is formed by the reaction of pyridoxal and amino acids, labelled with a radionuclide, in pyrogen-free water, the reaction product being adjusted to a pH of 8 to 9 and then autoclaved and cooled to produce a sterile, pyrogen-free non-antigenic solution for injection for biliary scanning.

Frank et al., in U.S. Pat. No. 4,193,979 disclose complexes of the compound sodium 3-[[2-(2-methyl-5-nitro-1H-imidazol-1-yl)ethyl] -amino]carbonyl]-2-pyridine carboxylic acid (and related compounds) with radioactive technetium-99m. These complexes are disclosed for use as radiopharmaceutical imaging agents, and in particular, these complexes are useful as gallbladder and liver imaging agents.

Thakur, in U.S. Pat. No. 4,443,426, discloses an agent for labelling blood cells comprising a complex of a radioactive metal (e.g., Tc-99m) with an N-oxide of pyridine. This complex is disclosed for use for the in vivo imaging of blood cells for diagnostic purposes.

Feld et al., in U.S. Pat. No. 4,714,065, disclose technetium-99m labeled dioxime complexes for imaging the myocardium, brain and hepatobiliary systems of humans and other mammalian species.

Srivastava et al., in U.S. Pat. No. 4,764,598, disclose a class of radiolabeled compounds as imaging agents with rapid brain uptake, good brain/blood radioactivity ratios, and long retention times. The imaging agents comprise radioiodinated aromatic amines attached to dihydropyridine carriers.

Benedict et al., in U.S. Pat. No. 4,830,847, disclose diphosphonate-derived macromolecules, such as proteins, as being suitable for use as technetium-99m based scanning agents. The scanning agents are prepared by combining Tc-99m in a +3, +4 and/or +5 oxidation state with the diphosphonate derivatized macromolecules. Also disclosed are pharmaceutical compositions containing these diphosphonate derivatized macromolecules and methods for scintigraphic imaging using these diphosphonate derivatized macromolecules labeled with Tc-99m.

Rocklage et al., in U.S. Pat. No. 4,842,845, disclose radioactive metal ion chelates of N,N'-bis-(pyridoxal-5-phosphate)-alkylenediamine- N,N'-diacetic acids, N,N'-bis-(pyridoxal-5-phosphate)-1,2-cycloalkylenediamine-N,N-diacetic acids, and N,N-bis-(pyridoxal-5-phosphate)-1,2-arylenediamine-N,N'-diacetic acids, the corresponding monophosphate compounds and monoacetic acid compounds, and their salts and esters. Preferred agents are technetium-99m and indium-111 ion chelates of N,N'-bis-pyridoxal-5- phosphate)ethylenediamine-N,N'-diacetic acid, N,N'-bis-(pyridoxal-5-phosphate)trans-1,2-cyclohexylene-diamine-N,N'-diacetic acid, N,N'-bis-(pyridoxal-5-phosphate)-trans-1,2- arylenediamine-N,N'-diacetic acid, and the soluble calcium salts thereof.

Benedict et al., in U.S. Pat. No. 5,011,913, disclose diphosphonate derivatized macromolecules, such as proteins, suitable for use as technetium-99m-based scanning agents. The scanning agents are prepared by combining Tc-99m in a +3, +4 and/or +5 oxidation state with the diphosphonate derivatized macromolecules. Also disclosed are pharmaceutical compositions containing these diphosphonate derivatized macromolecules and methods for scintigraphic imaging using these diphosphonate derivatized macromolecules labeled with Tc-99m.

The following literature references relate to heterocyclic complexes with various metals and contain disclosures of pyridinone or hydroxypyridinone complexes of metals such as aluminum, gallium or indium (but not technetium):

M. M. Finnegan et al., *J. Amer. Chem. Soc.*, 108, 5033–5035 (1986) disclose a neutral water-soluble aluminum complex of 3-hydroxy-2-methyl-4H-pyran-4-one.

Kontoghiorghes et al., *Inorganica Chimica Acta*, 136, L11–L12 (1987) disclose the synthesis of iron chelators 1-alkyl-3-hydroxy-2-methylpyrid-4-ones.

Finnegan et al., *Inorg. Chem.*, 26, 2171–2176, (1987) disclose neutral water-soluble post-transition metal chelate complexes of medical interest, specifically aluminum and gallium tris(3-hydroxy-4-pyronates).

Nelson et al., *J. Am. Chem. Soc.*, 109, 4121–4123 (1987) disclose the exoclathrate $Al(C_7H_8NO_2)^{3-} \cdot 12H_2O$.

Nelson et al., *Inorg. Chem.*, 27, 1045–1051 (1988) disclose aluminum and gallium compounds of 3-hydroxy-4-pyridinones, their synthesis, characterization, and crystallography of these biologically active complexes.

Matsuba et al., *Inorg. Chem.*, 27, 3935–3939 (1988) disclose neutral water-soluble indium complexes of 3-hydroxy-4-pyrones and 3-hydroxy-4-pyridinones.

Clevette et al., *Inorg. Chem.*, 28, 2079–2081 (1989) disclose the complexation of aluminum with N-substituted 3-hydroxy-4-pyridinones.

Nelson et al., *Inorg. Chem.*, 28, 3153–3157 (1989) disclose aluminum and gallium complexes of 1-ethyl-3-hydroxy-2-methyl-4-pyridinone as a new exoclathrae matrix.

Clevette et al., *Inorg. Chem.*, 29, 667–672 (1990) disclose the solution chemistry of gallium and indium 3-hydroxy-4-pyridinone complexes in vitro and in vivo.

Zhang et al., *Inorg. Chem.*, 30, 509–515 (1991) disclose lipophilic coordination compounds comprising aluminum, gallium, and indium complexes of 1-Aryl-3-hydroxy-2-methyl-4-pyridinones.

Finally, maltol and Kojic acid have recently been complexed with Tc-99m to form cationic scintigraphic complexes. See, Kanvinde et al., *J. Nuclear Med.*, 31:908, Abst. No. 866 (1990).

None of the above cited patents or publications either teach or suggest the existence of the novel cationic technetium radiopharmaceutical complexes of the present invention or that such complexes would be useful diagnostic imaging agents.

DETAILED DESCRIPTION OF THE INVENTION

Cationic technetium-99m complexes of N-substituted, 3-hydroxy-4-pyridinone ligands are new and are useful as radiopharmaceutical diagnostic substances as scintigraphic imaging agents. The novel cationic technetium complexes of the present invention are complexes of technetium-99m (also referred to as Tc-99m or $^{99m}$Tc) and N-substituted 3-hydroxy-4-pyridinones. The technetium-99m complexes of the present invention can be represented by the formula:

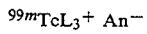

$$^{99m}TcL_3^+ \; An^-$$

where L represents ligands having the structure:

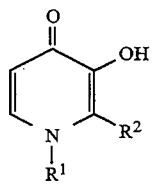

wherein:

$R^1$ is hydrogen or is selected from the group consisting of $C_1$ to $C_{20}$ alkyl; $C_3$ to $C_{12}$ cycloalkyl; $C_7$ to $C_{24}$ aralkyl; $C_2$ to $C_{16}$ alkyl ethers, thioethers, ketones or esters; $C_7$ to $C_{27}$ aralkyl ethers;

$R^2$ is hydrogen or is a $C_1$ to $C_4$ lower alkyl radical selected from the group consisting of methyl, ethyl, propyl, isopropyl, butyl, isobutyl, sec-butyl and tert-butyl; and $An^-$ is a pharmacologically suitable counterion.

The cationic technetium complexes of the present invention are useful as diagnostic agents in mammalian, especially human, scintiscanning. More particularly, the cationic technetium complexes of the present invention are useful for the imaging of human body components selected from the group consisting of the heart, lungs, liver, and blood cells, depending upon the relative lipophilicity of the complex.

Several factors govern the lipid solubility (or lipophilicity) of radiopharmaceuticals, and the degree of lipophilicity of a particular complex is one means well known to those skilled in this art for directing the complex to particular organs or body components. These factors include the relative hydrophilic and/or hydrophobic nature of the ligands, the charge on the complex (+, −, or neutral), steric and other size or weight related features of the ligands, and the like. Several common chemical functional groups employed in ligands, and their effect on lipophilicity are the following:

| Decrease hydrophilic groups, e.g.: | Increase hydrophobic groups, e.g.: |
|---|---|
| —OH | aromatic rings |
| —COOH | -alkyl groups |
| —(C=O)— | —C=C— |
| —PO$_4$ | —C≡C— |
| —NH$_2$ | -halogen |
| —SOOH | —SH |
| —SONH$_2$ | |
| —OCH$_3$ | |

By combining one or more hydrophilic and hydrophobic groups as substituents on a particular ligand structure, for example, as substituents on or as part of the groups comprising $R^1$ and $R^2$, one can construct complexes tailoring the relative lipophilicity of the complex and affecting the affinity for a desired target organ or body component in a manner well known to those skilled in this art. Routine imaging will demonstrate the effect of the particular groups.

One preferred process for utilizing complexes of the present invention comprises intravenously injecting into a patient, an effective amount of the complex in a sterile, pyrogen-free, non-antigenic carrier suitable for intravenous injection and thereafter scanning the body component or the particular organ to be imaged with a suitable scintiscanning means.

Thus, one preferred embodiment of the present invention is an injectable solution comprising an effective amount of the cationic technetium complex of the present invention in a sterile, pyrogen-free, non-antigenic carrier such as, for example, physiologically acceptable saline solution or deoxygenated, sterile, pyrogen-free water.

DEFINITIONS

As used herein, the term "$C_1$ to $C_{20}$ alkyl" is used to define a radical containing from 1 to 20 carbon atoms, which may be linear or branched, and which may include one or more sites of unsaturation, i.e., one or more double and/or triple bonds located between two adjacent carbon atoms.

As used herein, the term "$C_3$ to $C_{12}$ cycloalkyl" is used to define a carbocyclic radical containing from 3 to 12 carbon atoms, which may include one or more sites of unsaturation, i.e., one or more double and/or triple bonds located between two adjacent carbon atoms.

As used herein, the term "$C_7$ to $C_{24}$ aralkyl" is used to define a radical which includes both an aromatic radical of 6 to 14 carbon atoms ("At") and at least one alkyl radical of 1 to 10 carbon atoms, which may include one or more sites of unsaturation, i.e., one or more double and/or triple bonds located between two adjacent carbon atoms. Aralkyl is used herein to designate both of the following structural attachment possibilities for this ligand:

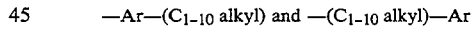

—Ar—(C$_{1-10}$ alkyl) and —(C$_{1-10}$ alkyl)—Ar

As used herein, the terms "$C_2$ to $C_{16}$ alkyl ethers, thioethers, ketones or esters" are used to define radicals having a formula of the type, for example:

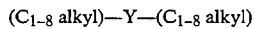

(C$_{1-8}$ alkyl)—Y—(C$_{1-8}$ alkyl)

wherein Y is either —O— (ethers), —S— (thioethers), —(C=O)— (ketones), or —O(C=O)— (esters), and each C$_{1-8}$ alkyl radical may independently be linear or branched, and may include one or more sites of unsaturation, i.e., one or more double and/or triple bonds located between two adjacent carbon atoms. Either end of the radical may serve as the attachment site.

As used herein, the term "$C_7$ to $C_{27}$ araalkyl ethers" includes both an aromatic radical of 6–14 carbon atoms and an alkyl ether, of the structure:

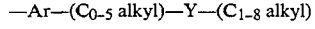

—Ar—(C$_{0-5}$ alkyl)—Y—(C$_{1-8}$ alkyl)

wherein Y is O or S and the 0–5 and 1–8 carbon atom alkyl radical may be linear or branched and may include one or more sites of unsaturation, i.e., one or more double and/or triple bonds between two adjacent carbon atoms.

The radicals defined above may have substituents, such as those hydrophilic and hydrophobic substituents listed above, for any one or more of the hydrogen atoms on either the aryl or alkyl components or on both.

DESCRIPTION OF THE PREFERRED EMBODIMENTS

As described above, preferred cationic complexes of the present invention can be represented by the formula:

$^{99m}TcL_3{}^+$      (I)

where L represents ligands having the structure:

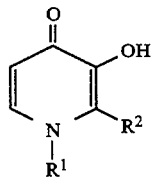

wherein, preferably:
R$^1$ is selected from the group consisting of:
(a) hydrogen;
(b) C$_1$ to C$_{20}$ alkyl radicals, preferably C$_1$ to C$_{12}$ alkyl radicals, and most preferably C$_1$ to C$_8$ alkyl radicals;
(c) C$_3$ to C$_{12}$ cycloalkyl radicals, preferably C$_3$ to C$_6$ cycloalkyl radicals;
(d) C$_7$ to C$_{24}$ aralkyl radicals, preferably C$_7$ to C$_{12}$ aralkyl radicals;
(e) C$_2$ to C$_{16}$ alkyl ethers, preferably C$_4$ to C$_8$ alkyl ethers;
(f) C$_2$ to C$_{16}$ alkyl thioethers, preferably C$_4$ to C$_8$ alkyl ethers;
(g) C$_2$ to C$_{16}$ alkyl ketones, preferably C$_4$ to C$_8$ alkyl ketones;
(h) C$_2$ to C$_{16}$ alkyl esters, preferably C$_4$ to C$_8$ alkyl esters; and
(i) C$_7$ to C$_{27}$ aralkyl ethers, preferably C$_7$ to C$_{12}$ aralkyl ethers; and
R$^2$ is hydrogen or a C$_1$ to C$_4$ lower alkyl radical selected from the group consisting of methyl, ethyl, propyl, isopropyl, butyl, isobutyl, sec-butyl and tert-butyl. Preferably, R$^2$ is methyl or ethyl, most preferably, R$^2$ is methyl.

Examples of C$_1$ to C$_{20}$ alkyl radicals include, ethyl, ethyl, propyl, isopropyl, n-butyl, iso-butyl, sec-butyl, tert-butyl, pentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and the like.

Examples of C$_1$ to C$_{20}$ alkyl radicals when one or more double and/or triple bonds are present therein include, ethylene, propylene, isomeric butylenes, isomeric amylenes, acetylene, propyne, dimethylacetylene, ethyl acetylene, butadienes, isoprene, and the like.

Examples of C$_3$ to C$_6$ cycloalkyl radicals include, cyclopropyl, cyclobutyl, cyclopentyl, cyclohexyl, cyclohexenyl, cyclohexadienyl, and the like.

Examples of C$_6$ to C$_{14}$ aryl radicals include, phenyl, naphthyl, anthryl, biphenyl and the like.

Examples of C$_7$ to C$_{20}$ aralkyl radicals include, benzyl, tolyl, o-xylyl, m-xylyl, p-xylyl, ethylbenzyl, propylbenzyl, isopropylbenzyl, ethylnaphthyl, and the like.

Examples of C$_7$ to C$_{27}$ aralkyl ether radicals include para-methoxyphenyl, ethoxyphenyl, methoxynaphthyl, and the like.

The ligands of the present invention may be readily prepared using conventional synthetic methods. For example, when R$^2$ is methyl, a convenient starting material for the formation of ligands with variable R$^1$ substituents is maltol, which has the structure:

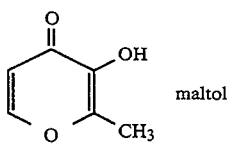 maltol

The direct condensation reaction of maltol and an amine having the structure R$^1$—NH$_2$ yields the ligand having the formula:

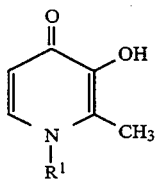

When R$^2$ is not methyl, other conventional organic synthetic methods, readily available to those of skill in the art of organic synthesis, may be employed to produce the desired ligands.

As described above, the ligands of the present invention are useful as scintigraphic imaging agents when complexed or chelated with technetium-99m. In general, the complex is prepared by the reduction of an aqueous solution of heptavalent (+7) $^{99m}$Tc pertechnetate ion (e.g., Na$^{99m}$TcO$_4$) with a suitable reducing agent capable of reducing the ($^{99m}$TcO$_4{}^-$), in the presence of the ligand. For preferred complexes having the structure of formula I above, the technetium is reduced to the tetravalent (+4) state. Suitable reducing agents include stannous (i.e., Sn$^{2+}$) ions or bisulfite (S$_2$O$_5{}^{2-}$) ions. Such ions are commonly provided from inorganic salts, e.g., stannous chloride and sodium bisulfite, respectively.

The present complex, suitable for in vivo administration, is generally formed using physiologically acceptable media in a manner well within the ordinary skill of those conversant with this art. For example, the ligand, optionally with the addition of pharmaceutically acceptable carriers and/or excipients, is suspended or dissolved in an aqueous medium along with a reducing agent in a non-pyrogenic vial, and then the solution or suspension is lyophilized and the vial is sterilized. The lyophilized material is reconstituted with Tc-99m pertechnetate eluted in saline from a commercial generator. Optionally, the vial is then heated in a water bath.

Suitable additives include, for example, physiologically biocompatible buffers (as, for example, tromethamine hydrochloride), slight additions of other chelating agents (as for example, diethylenetriaminepentacetic acid) or, calcium salts (for example, calcium chloride, calcium ascotbate, calcium gluconate or calcium lactate) and pharmaceutically acceptable fillers such as mannitol.

The usual mode for administering complexes of this type, for use as radioimaging agents, is by intravenous administration. Intravenous solutions must be sterile, free from physiologically unacceptable agents, and preferably are isotonic or iso-osmotic to minimize irritation or other adverse effects upon administration.

Suitable vehicles for intravenous administration include, for example, aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in *Remington's Pharmaceutical Sciences*, 15th Ed., Mack Publishing Co. pp. 1405–1412 and 1461–1487 (1975) and *The National Formulary XIV*, 14th Ed. Washington: American Pharmaceutical Association (1975), the contents of which are hereby incorporated by reference.

Such solutions can contain preservatives, antimicrobial agents, buffers and antioxidants conventionally used in parenteral solutions. Excipients and other additives must be selected to be compatible with the chelates, so as not to interfere with the manufacture, storage or use of the products, as is well known by those skilled in the art.

The technetium-99m concentration employed in the diagnostic preparations of this inventory is typically in the range from about 0.01 to 100 mCi/ml, preferably from about 1 to 50 mCi/ml, and most preferably from about 2 to 25 mCi/ml, after being complexed with the ligand.

The complexes of this invention are administered to patients for imaging in amounts which are sufficient to yield the desired image. Such doses are typically determined by clinical trials in accord with well established practices known to those possessing ordinary skill in this art. For example, one commercial product, Cardiolite® (a complex of the formula Tc-99m[MIBI]6, where MIBI is 2-methoxy isobutyl isonitrile), has a Tc-99m concentration of 25 mCi/ml, which after administration to a patient (~70 kg) in accord with the package insert results in a dosage of about 0.35 mCi/kg.

Methods of using the present radiopharmaceutical agents for imaging, and the equipment and methods for imaging are described by Alaraki, N., et al., *Fundamentals of Nuclear Medicine*, New York: The Society of Nuclear Medicine, Inc. (1984); *The Chemistry of Radiopharmaceuticals*, Heindel, N. et al., Editors, Chicago; Masson Publishing (1978); and *Radiopharmaceuticals: Progress and Clinical Perspectives*, Fitzberg, A. Editor, Boca Raton, Fla.: CRC Press (1986), and the publications cited therein. The contents of each of these publications and the reference citations included therein are incorporated herein by reference.

While intravenous administration is preferred, the complexes of the present invention may, if desired, be administered by other means in accord with established practices for imaging the particular body components desired.

The complex of the present invention is typically prepared when required for use, due to the short half-life of technetium-99m. Thus, another embodiment of the present invention comprises a kit suitable for the preparation of the complex of the present invention.

A typical kit comprises at least one sterilized vial containing sufficient ligand to complex with the technetium-99m, in a suitable form, preferably lyophilized, for the preparation of an injectable formulation. The vial also contains an excess amount of a suitable reducing agent and any other excipients desired. Tc-99m, obtained from a commercial generator, is added to the ligand vial. The formation of the complex of the present invention occurs in situ in the vial upon mixing. If necessary or desired, heating of the vial, e.g., in a water bath, may be used to speed up the reaction.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius. The reagent chemicals employed herein were obtained from commercial sources, e.g., the Aldrich Chemical Co., St. Louis, Mo. The preferred reducing agent used herein, commercial sodium bisulfite (Aldrich No. 24,397-3) contains both $HSO_3^-$ (hydrogen sulfite) and $S_2O_5^{2-}$ (metabisulfite) ions.

The synthetic route to the 3-hydroxypyrid-4-one ligands shown below was adapted in part from Kontoghorghes, *Inorganica Chimica Acta*, 136 (1987) L11–L12.

EXAMPLE 1

1-Isopropyl-3-Hydroxy-2-Methylpyrid-4-One

1-Isopropyl-3-hydroxy-2-methylpyrid-4-one was prepared by refluxing 3-hydroxy-2-methylpyrid-4-one (Maltol) (10.0 g) with 3 equivalents of isopropylamine (99%) in 200 ml of water for 8 hours. Decolorizing charcoal was added after refluxing and the mixture was stirred for 0.5 hours. The mixture was then filtered through a medium frit filter containing 0.5 inches of Celite. The filtered solution was then concentrated in vacuo (rotary evaporator) to remove the water and excess amine, leaving a dark thick oil. The oil was then dissolved in minimal amounts of hot acetone and filtered (repeatedly) through a medium frit filter. Brownish crystals (product) remained on the frit and these were then washed (3X) with 1 ml portions of hot acetone to obtain white crystals. m.p. 239°–242 ° C.

EXAMPLE 2

1-Isobutyl-3-Hydroxy-2-Methylpyrid-4-One

1-Isobutyl-3-hydroxy-2-methylpyrid-4-one was prepared in a manner similar to that used in Example 1 for the preparation of 1-isopropyl-3-hydroxy-2-methylpyrid-4-one. Again, 3 equivalents of amine (isobutylamine—99% ) was employed, and the reflux conditions were the same. The product was again crystallized from hot acetone, which yielded pure crystals of product. m.p. 170°–171 ° C.

EXAMPLE 3

1-Ethyl-3-Hydroxy-2-Methylpyrid-4-One

1-Ethyl-3-hydroxy-2-methylpyrid-4-one was prepared by dissolving 10.0 g of 3-hydroxy-2-methylpyr-4-one (Maltol) and 3 equivalents of ethylamine (70%) in 200 ml of water. The reaction mixture was refluxed for 10 hours at which time it was black in color. Decolorizing charcoal was then added to the mixture and it was stirred an additional 0.5 hours. The mixture was then filtered through a fine frit and the filtrate was concentrated in vacuo to remove the water and excess amine. The resulting brown crystals were recrystallized using hot methanol which yielded white needles of pure product. m.p. 204°–205 ° C.

EXAMPLE 4

1-Benzyl-3-Hydroxy-2-Methylpyrid-4-One

1-Benzyl-3-hydroxy-2-methylpyrid-4-one was prepared in a manner similar to that used in the previous examples. Again, 3 equivalents of amine, namely benzylamine (99%) were employed. The solution was then refluxed for 4 hours at which time the mixture was dark orange in color. This mixture was cooled to about 0° C. After 24 hours at about 0° C., the mixture was removed and the aqueous layer was decanted off. The remaining solids were crystallized from hot methanol which gave pure product which was white in color. m.p. 205°–207° C.

EXAMPLE 5

1-(3-Butoxypropyl)-3-Hydroxy-2-Methylpyrid-4-One 1-(3-Butoxypropyl)-3-hydroxy-2-methylpyrid-4-one was prepared by dissolving 10.0 g maltol and 3 equivalents of 3-butoxypropylamine in 200 ml of water. The mixture was refluxed for 72 hours, decolorizing charcoal was added and the mixture was stirred for an additional 0.5 hours. The mixture was filtered through a coarse frit containing 0.5 inches of Celite, and the filtrate was concentrated in vacuo to remove the water and excess amine. The remaining oil was crystallized from ether, yielding crystals of pure product.

EXAMPLE 6

1-Cyclohexyl-3-Hydroxy-2-Methylpyrid-4-One

1-Cyclohexyl-3-hydroxy-2-methylpyrid-4-one was prepared by dissolving 10.0 g of 3-hydroxy-2-methylpyr-4-one (Maltol) and 3 equivalents (~27 ml) of cyclohexylamine (99+ %) in 200 ml of water. Decolorizing charcoal was added and the mixture was stirred for 0.5 hours. The aqueous mixture was filtered through a course frit then concentrated in vacuo, leaving an oily residue. Crystallization from hot water yielded crystals of the desired product. m.p. 199° C.

Table 1 below provides physical data of the ligands prepared in the preceding Examples.

TABLE 1

Proton NMR chemical shift data for pyridinone ligands at 270 MHz (ppm):

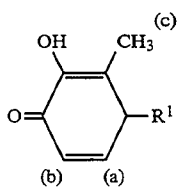

| $R^1$ | (a) | (b) | (c) | (d) | (e) | (f) | (r) |
|---|---|---|---|---|---|---|---|
| $CH_2{}^dCH_3{}^e$ | 6.37 | 7.21 | 2.37 | 3.90 | 1.37 | | |
| $CH^d(CH_3)_2{}^e$ | 6.43 | 7.34 | 2.40 | 4.45 | 1.42 | | |
| $CH_2{}^dCH^e(CH_3)_2{}^f$ | 6.35 | 7.16 | 2.36 | 3.64 | 2.00 | 0.93 | |
| $C_6H_{11}{}^r$ | 6.42 | 7.36 | 2.41 | | | | 1.17–1.98 |
| $CH_2{}^dC_6H_5{}^r$ | 6.44 | 7.00 | 2.27 | 5.08 | | | 7.25–7.40 |

$^{13}$C-NMR chemical shift data for Example 2 at 67 MHz (ppm):

TABLE 1-continued

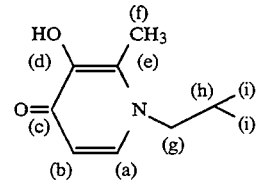

| (a) | (b) | (c) | (d) | (e) | (f) | (g) | (h) | (i) |
|---|---|---|---|---|---|---|---|---|
| 11.07 | 137.8 | 169.4 | 146.2 | 128.4 | 19.5 | 60.9 | 29.6 | 11.9 |

Selected infrared absorption bands (cm$^{-1}$) for Example 2:

| OH | CH, aliphatic | C=O | ring |
|---|---|---|---|
| 3259* | 2850–2990 | 1652 | 1462–1620 |

*broad band

Proton NMR chemical shift data for Example 5 at 270 MHz (ppm):

1-(3-butyoxypropyl)-3-hydroxy-2-methylpyrid-4-one

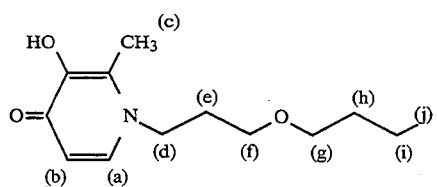

| (a) | (b) | (c) | (d) | (e) | (f) | (g) | (h) | (i) | (j) |
|---|---|---|---|---|---|---|---|---|---|
| 7.25 | 6.38 | 2.39 | 4.00* | 1.94 | 4.00* | 3.47 | 1.55 | 1.37 | 0.93 |

*Proton shifts for the two carbons overlap at this point.

EXAMPLE 7

Synthesis of Technetium-99m N-Alkyl-3-Hydroxypyrid-4-One Complexes

The $^{99m}$Tc-pyridinone complexes using various ligands of the present invention may be prepared as described below.

$^{99m}$Tc-pyridinone complexes with representative ligands of the present invention were prepared by dissolving about 4 mg of neat ligand, 30 mCi of $^{99m}$TcO$_4$-generator eluate, and 15 mg sodium bisulfite in from about 1–2 ml of a 20% (v/v) ethanol/saline solution. This solution was then heated at 100° C. for 15 min. The radiochemical purity of each complex was greater that 90% and was maintained for greater than about 4 hours.

The complex may also be formed using tin(II) chloride instead of sodium bisulfite.

Table 2 below provides physical data of complexes prepared as set forth above.

TABLE 2

Physical Data of Representative Tc-99m Complexes

| $R^1$ | TLC $R_f$ | HPLC $R_t$ | Charge |
|---|---|---|---|
| —$C_2H_5$ | 0.86 | 3.30 | + |
| i-$C_3H_7$ | 0.78 | 7.28 | + |
| i-$C_4H_9$ | 0.67 | 10.59 | + |
| —$C_6H_{11}$ | 0.53 | 25.57 | + |
| —$CH_2C_6H_5$ | 0.61 | 16.27 | + |
| —$(CH_2)_3O(CH_2)_3CH_3$ | 0.61 | 19.86 | + |
| -p-methoxyphenyl | 0.64 | 19.06 | + |

HPLC: Hamilton PRP-1 column, gradient method 40/60 to 80/20 CH$_3$CN (0.1% TFA)/Water (0.1% TFA) over 20 min.
TLC: C$_{18}$ reverse phase plates, 4:3:2:1 solvent mixture (CH$_3$CN: MeOH: NH$_4$OAc: THF)
Electrophoresis: Whatman 31 ET CHR paper, 0.70 MeOH/0.025M phosphate buffer (pH 7), 250 V, 30 min.

EXAMPLE 8

A procedure for determining a mammalian biodistribution profile of complexes as prepared in accord with Example 7 is described below.

Nine (9) male guinea pigs (250–500 g) were anesthetized with sodium phenobarbitol. Injection of a sterile, non-pyrogenic solution of the complex was via the jugular vein. The injected dosage was varied according to the weight of the animal as necessary to provide a dose approximately 20–25 mCi/kg.

Three animals were sacrificed at each time interval; i.e., 5 min, 15 min, and 60 min after injection. The heart, lungs and liver were then dissected and counted for $^{99m}Tc$ as were the blood and the remaining carcass. Average counts from each organ were converted to a percentage of injected dose per gram of tissue weight (% i.d./g organ). The biodistribution of representative Tc-99m complexes of the invention is presented in Table 3 below.

TABLE 3

Guinea Pig Biodistribution of Tc-99 Complexes of Formula (I)
($R^2$ = $CH_3$) (% i.d./g organ)

| | | $R^1$ = $CH_2CH_3$ | $R^1$ = $CH_2CH(CH_3)_2$ | $R^1$ = $CH_2C_6H_5$ | $R^1$ = $C_6H_{11}$ |
|---|---|---|---|---|---|
| Heart: | t = 5 min | 0.21 ± .02 | 0.47 ± .04 | 0.538 ± .04 | 0.04 ± .001 |
| | t = 15 | 0.15 ± .03 | 0.46 ± .04 | 0.704 ± .13 | 0.03 ± .005 |
| | t = 60 | 0.06 ± .009 | 0.40 ± .05 | 0.663 ± .08 | 0.04 ± .002 |
| Lung: | t = 5 min | 0.35 ± .03 | 0.45 ± .05 | 0.273 ± .02 | 1.10 ± .33 |
| | t = 15 | 0.24 ± .08 | 0.33 ± .07 | 0.316 ± .06 | 0.50 ± .09 |
| | t = 60 | 0.10 ± .02 | 0.19 ± .02 | 0.260 ± .02 | 0.36 ± .04 |
| Liver: | t = 5 min | 0.79 ± .12 | 1.85 ± .35 | 3.078 ± .49 | 1.08 ± .16 |
| | t = 15 | 0.69 ± .06 | 2.19 ± .26 | 2.718 ± .56 | 0.47 ± .05 |
| | t = 60 | 0.87 ± .11 | 1.49 ± .29 | 3.078 ± .59 | 0.23 ± .01 |
| Blood: | t = 5 min | 0.50 ± .03 | 0.27 ± .31 | 0.168 ± .03 | 0.005 ± .001 |
| | t = 15 | 0.31 ± .10 | 0.07 ± .01 | 0.144 ± .02 | 0.003 ± .001 |
| | t = 60 | 0.11 ± .02 | 0.13 ± .01 | 0.080 ± .01 | 0.001 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Cationic complexes of the formula:

$$^{99m}TcL_3^+$$

where L represents ligands having the structure:

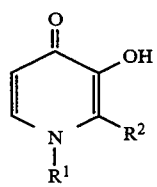

wherein:
R$^1$ is hydrogen or is selected from the group consisting of C$_1$ to C$_{20}$ alkyl; C$_3$ to C$_{12}$ cycloalkyl; C$_7$ to C$_{24}$ aralkyl; C$_2$ to C$_{16}$ alkyl ethers, thioethers, ketones or esters; C$_7$ to C$_{27}$ aralkyl ethers;
R$^2$ is hydrogen or is a C$_1$ to C$_4$ lower alkyl radical selected from the group consisting of methyl, ethyl, propyl, isopropyl, butyl, isobutyl, sec-butyl and tert-butyl.

2. The complex of claim 1, wherein R$^1$ is a C$_1$ to C$_{12}$ alkyl radical.

3. The complex of claim 1, wherein R$^1$ is a C$_1$ to C$_8$ alkyl radical.

4. The complex of claim 1, wherein R$^1$ is a C$_3$ to C$_6$ cycloalkyl radical.

5. The complex of claim 1, wherein R$^1$ is a C$_7$ to C$_{12}$ aralkyl radical.

6. The complex of claim 1, wherein R$^1$ is a C$_4$ to C$_8$ alkyl ether radical.

7. The complex of claim 1, wherein R$^1$ is a C$_7$ to C$_{12}$ aralkyl ether radical.

8. The complex of claim 7, wherein R$^1$ is paramethoxyphenyl.

9. A radioactive composition comprising a solution containing a pharmacological carrier and cationic complex of the formula:

$$^{99m}TcL_3^+$$

where L represents ligands having the structure:

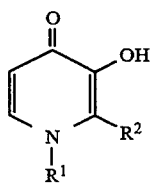

wherein:
R$^1$ is hydrogen or is selected from the group consisting of C$_1$ to C$_{20}$ alkyl; C$_3$ to C$_{12}$ cycloalkyl; C$_7$ to C$_{24}$ aralkyl; C$_2$ to C$_{16}$ alkyl ethers, thioethers, ketones or esters; C$_7$ to C$_{27}$ aralkyl ethers; and
R$^2$ is hydrogen or is a C$_1$ to C$_4$ lower alkyl radical selected from the group consisting of methyl, ethyl, propyl, isopropyl, butyl, isobutyl, sec-butyl and tert-butyl.

10. A composition suitable for intravenous injection comprising an injectable solution containing a complex of the formula:

$$^{99m}TcL_3^+$$

where L represents ligands having the structure:

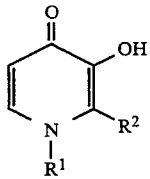

wherein:
R[1] is hydrogen or is selected from the group consisting of $C_1$ to $C_{20}$ alkyl; $C_3$ to $C_{12}$ cycloalkyl; $C_7$ to $C_{24}$ aralkyl; $C_2$ to $C_{16}$ alkyl ethers, thioethers, ketones or esters; $C_7$ to $C_{27}$ aralkyl ethers; and R[2] is hydrogen or is a $C_1$ to $C_4$ lower alkyl radical selected from the group consisting of methyl, ethyl, propyl, isopropyl, butyl, isobutyl, sec-butyl and tert-butyl.

* * * * *